United States Patent [19]
Hsieh

[11] Patent Number: 5,265,142
[45] Date of Patent: Nov. 23, 1993

[54] IMAGE RECONSTRUCTION TECHNIQUE FOR A COMPUTER TOMOGRAPHY SYSTEM

[75] Inventor: Jiang Hsieh, Waukesha, Wis.

[73] Assignee: General Electric Company, Milwaukee, Wis.

[21] Appl. No.: 880,255

[22] Filed: May 8, 1992

[51] Int. Cl.⁵ ............................................. G01N 23/06
[52] U.S. Cl. ........................................ 378/4; 378/9; 378/11; 378/19
[58] Field of Search ................... 378/4, 9, 10, 11, 12, 378/14, 15, 19, 20

[56] References Cited
U.S. PATENT DOCUMENTS

| | | | |
|---|---|---|---|
| 4,171,476 | 10/1979 | Waltham | 250/445 |
| 4,176,279 | 11/1979 | Schwierz et al. | 378/4 |
| 4,178,511 | 12/1979 | Hounsfield et al. | 250/445 |
| 4,637,040 | 1/1987 | Sohval et al. | 378/9 |
| 4,754,468 | 6/1988 | Mori | 378/10 |
| 5,173,852 | 12/1992 | Lonn | 378/9 |

*Primary Examiner*—David P. Porta
*Attorney, Agent, or Firm*—Quarles & Brady

[57] ABSTRACT

A computed tomography apparatus includes a gantry rotatable about an object being imaged, an X-ray source mounted on said gantry in opposing relationship to an array of X-ray detectors. An X-ray controller causing emission of X-rays from the X-ray source to shift between the two focal spots to produce first and second sets of projection data. X-rays are emitted from a first focal spot of the source while one projection of the object is acquired. Then the operation of the source is altered to emit X-rays from a second focal spot and the gantry is rotated by one-half the pitch of the detectors. Another projection is acquired at the new gantry position. Additional projections are acquired by alternately emitting the X-ray beam from the two focal spots and advancing the gantry by equivalent amounts between each acquisition. Data samples of the projections acquired by emission form the first focal spot are interleaved with data samples from projections made using the second focal spot to produce a resultant group of projections. An image is reconstructed from the resultant data array.

11 Claims, 3 Drawing Sheets

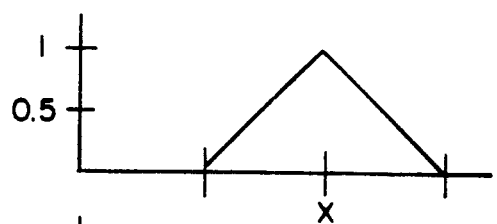
FIG.IA
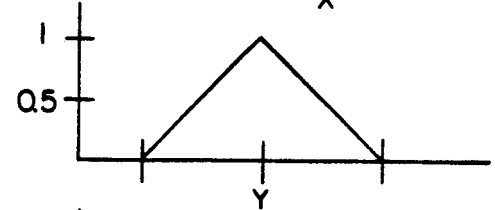
FIG.IB
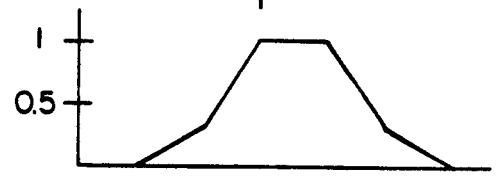
FIG.IC
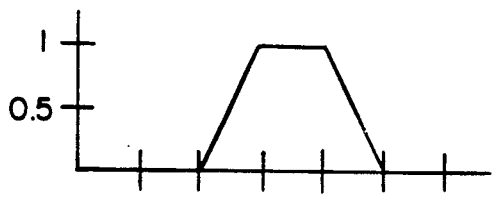
FIG.ID
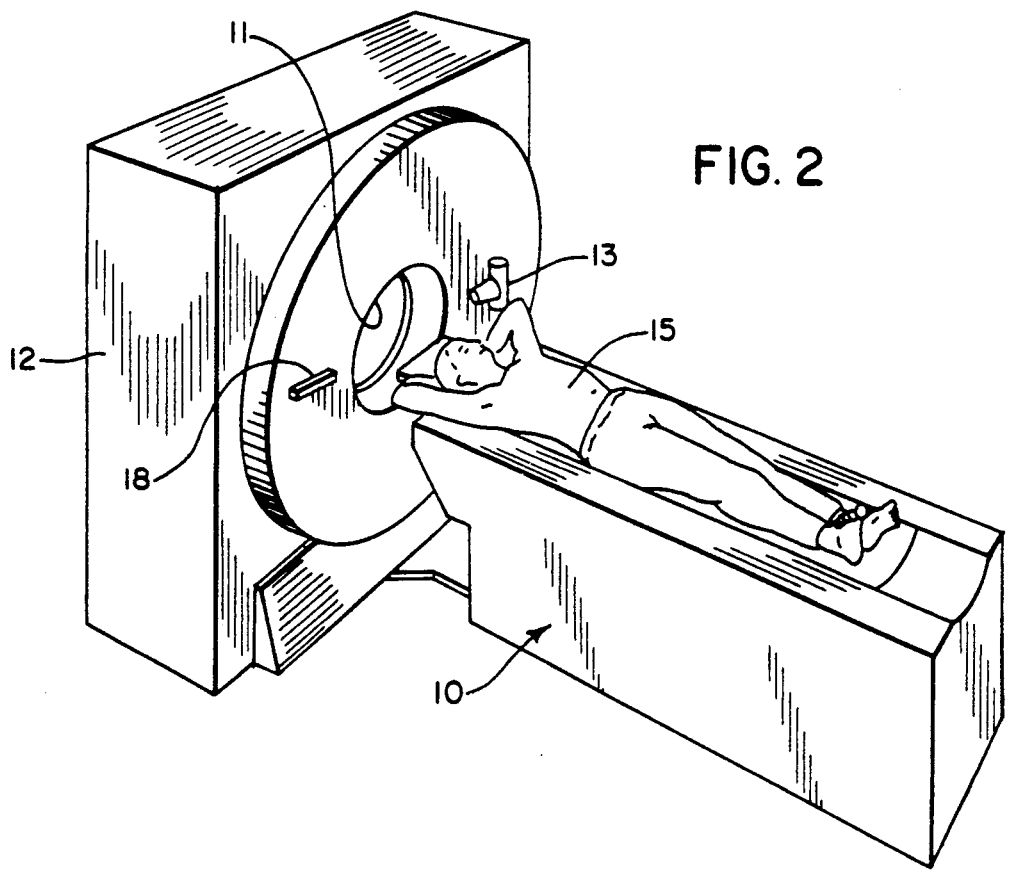
FIG. 2

IMAGE RECONSTRUCTION TECHNIQUE FOR A COMPUTER TOMOGRAPHY SYSTEM

BACKGROUND OF THE INVENTION

The present invention relates to computed tomography (CT) imaging apparatus; and more particularly, to techniques for reconstructing a image from X-ray attenuation data acquired by such apparatus.

In a computed tomography system, an X-ray source projects a fan-shaped pattern of beams, which is collimated to lie within an X-Y plane of a Cartesian coordinate system, termed the "imaging plane". The X-ray beams pass through the object being imaged, such as a medical patient, and impinge upon an array of radiation detectors. A beam of X-rays is defined as the radiation that strikes one of the detectors. The intensity of the transmitted radiation is dependent upon the attenuation of the X-ray beam by the object and each detector produces a separate electrical signal that is a measurement of beam attenuation. The attenuation measurements from all the detectors are acquired separately to produce an attenuation profile.

The source and detector array in a common type of CT system are rotated on a gantry within the imaging plane and around the object so that the angle at which the X-ray beam, intersects the object constantly changes. A group of X-ray attenuation measurements from the detector array at a given angle form a "projection" and a "scan" of the object comprises a set of projections made at different angular orientations during approximately a half or a full revolution of the X-ray source and detector. The gantry may stop or continue to move as the measurements are being made.

The resultant projections from the scan are used to reconstruct an image which reveals the anatomical structures in a slice taken through the object. The prevailing method for reconstructing image is referred to in the art as the filtered backprojection technique. This process converts the attenuation measurements from a scan into integers called "CT numbers" or "Hounsfield units", which are used to control the brightness of a corresponding pixel on a cathode ray tube display or on photographic film.

It is desirable to produce an image having as high resolution as possible. Spatial resolution of the reconstructed image is dependent, in part, on the width of each X-ray beam at the center of the imaged object. This beam width, which varies with the distance from the source and the detector, is determined primarily by the source width, the size of the focal spot on an anode of the X-ray tube, the geometry of the scanner, and the aperture of each detector. The averaging affect of a generally rectangular beam of width a, bandlimits the received image to a spatial frequency of 1/a and less.

The beam spacing, defined near the center of the imaged object and determined by the detector pitch, controls the spatial sampling frequency of the CT system. Given the spatial bandlimit of 1/a, the sampling frequency must be approximately 2/a, per the Nyquist sampling theorem, to avoid aliasing effects in the reconstructed image. The elimination of aliasing requires that the beam be sampled or read at distances separated by one-half the beam width. Ordinarily, the beam width is optimized to be substantially equal to the beam spacing and therefore sampling is ideally performed no less than twice per beam spacing. Henceforth referred to as "double sampling."

A conceptually simple way to accomplish double sampling is to shift the detectors one-half of their pitch after a first sample and then take a second sample. In this way each beam is sampled twice in its width (and spacing). Nevertheless, mechanical problems incident to rapidly and precisely moving the detectors by one-half their pitch (typically on the order of 1 mm) make this approach impractical.

Another method has been proposed as described in U.S. Pat. No. 5,173,852 entitled "Computed Tomography System with Translatable Focal Spot." This double sampling process is to wobble the X-ray source by an amount that will shift each beam by one-half its spacing. The wobbling is generally within the plane of rotation of the gantry and along the tangent to the gantry rotation. Wobbling of the X-ray source is easily accomplished electrostatically or electromagnetically without mechanical motion of the X-ray source. The source typically is an X-ray tube, in which an electron beam is accelerated against an anode at a focal spot to produce X radiation emanating from the focal spot. The focal spot may be moved on the surface of the anode by the use of deflection coils or electrodes within the X-ray tube which deflect the electron beam by the creation of a local magnetic or electrostatic field, as is well understood in the art.

Double sampling is performed by acquiring a second set of projections offset from the first set by one-half the pitch of the detectors. After acquiring a projection in the first set, a projection for the second set is acquired after the gantry moves an odd multiple of one-half the width of a detector (e.g. one half the width) and the focal spot is wobbled. The another projection is acquired for the first set after the gantry moves another amount equal to an odd multiple of one-half the width of a detector, or the full width of a detector from the location at which the previous projection for the first set was acquired. At this time the focal spot is wobbled back to its previous position on the anode surface. This alternating acquisition continues throughout the scan finally resulting in two interleaved sets of projections.

The two sets of projections were processed individually to reconstruct a pair of separate images. For example, conventional backprojection image reconstruction was performed on each set. The two reconstructed images then were added together to form a single image that is freer of aliasing artifacts than either image alone.

During the backprojection image reconstruction if a given picture element in the image lies directly on an X-ray beam extending between the focal spot and a detector in a given projection, then the projection data sample from the detector is used to form that picture element. However, if the picture element lies between two beams, then the samples from the detectors associated with those beams are used to form that picture element. For example, bi-linear interpolation is applied to the two detector samples to calculate a pseudo output that would have been produced by an imaginary detector if the pixel did lie directly on a beam of the X-ray beam. The two samples from the real detectors are weighted based on the relative position of the imaginary detector with respect to each real one.

This reconstruction technique introduces resolution degradation and a Moiré pattern into the image. The image degradation is apparent from a point spread function of the bi-linear interpolation process as graphically depicted in FIGS. 1A-1C. FIGS. 1A and 1B represent the point spread function for each set of projections with each vertical mark on the horizontal axes representing the center of a detector. Note that if the picture element is aligned with detector X or Y, the weighting factor is one for that detector and zero for the adjacent detectors. Likewise, if the picture element is aligned midway between two detectors, the outputs from each detector are weighted by one-half when forming the picture element. The resulting point spread function in FIG. 1C is produced by averaging the individual the point spread functions in FIGS. 1A and 1B, since the final step of the image reconstruction process averages the two reconstructed images. It is apparent from this graph that the point spread function behaves quite well at the center, but performs poorly at the boundaries. The long tails exhibited at the edges of the function contribute to the degradation of image resolution.

SUMMARY OF THE INVENTION

A computed tomography (CT) imaging apparatus has an X-ray source mounted on a gantry in opposition to an array of periodically spaced X-ray detectors. The gantry is capable of being rotated about an object being imaged to acquire a series of projections. Each projection is formed by signals produced by the detectors at different angular positions with respect to the object.

The gantry is rotated through an angular segment while X-rays are emitted from a first focal spot of the source. When the detectors rotate through an angular segment a first set of projections is acquired. A second set of projections is acquired while X-rays are emitted from a second focal spot as the detectors rotate through the angular segment. The second set of projections are interlaced with the first set of projections. In the preferred embodiment, projections in the two sets are alternately acquired as the detectors make a single pass through the angular segment. Alternatively, each set of projections can be acquired during separate passes through the angular segment.

The first and second sets of projections are combined into a resultant group of projections by interleaving data samples in the first set with data samples in the second set. An image then is reconstructed from the resultant group of projections using a technique such as filtered backprojection.

BRIEF DESCRIPTION OF THE DRAWINGS

FIGS. 1A, 1B and 1C represent point spread functions of a prior image reconstruction process, and FIG. 1D depicts the resultant point spread function of a process according to the present invention;

FIG. 2 is a pictorial view of a CT imaging system in which the present invention may be employed;

DETAILED DESCRIPTION OF THE INVENTION

Figure 3:
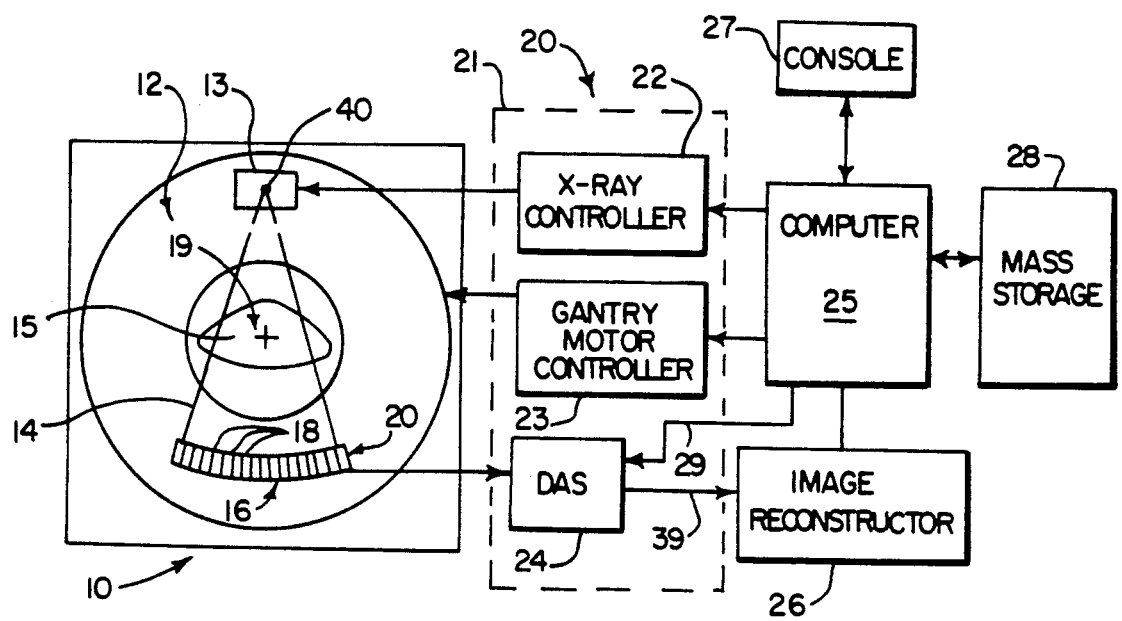
FIG. 3 is a block schematic diagram of a CT apparatus.

Referring to FIGS. 2 and 3, a computed tomography (CT) imaging system 10 includes a gantry 12 representative of a "third generation" CT scanner. The gantry 12 includes an X-ray source 13 oriented to project a fan-shaped beam pattern 14 of X-ray beams through imaged object 15 to detector array 16. The detector array 16 is formed by a number of detectors 18 abutted together at a periodic spacing P. Together the detectors 18 sense a projected image resulting from transmission of X-rays through the imaged object 15, such as a medical patient. The gantry 12 and the components mounted thereon revolve about a center point 19 located within the object 15.

A control mechanism 20 of the CT system 10 has gantry associated control modules 21 which include an X-ray controller 28 providing power and timing signals to the X-ray source 13, a gantry motor controller 23 that controls the rotational speed and position of the gantry 12, and a data acquisition system (DAS) 24 which samples projection data from detectors 18 and converts the data to digital words for subsequent computer processing.

The data acquisition system 24 filters, amplifies, digitizes and otherwise conditions a signal from each detector 18. The data output from the DAS 24 on line 39 is connected to image reconstructor 26 which receives the sampled and digitized projection data and performs high speed image reconstruction according to methods known in the art. The image reconstructor 26 is an array processor, such as one manufactured by Star Technologies, and includes a memory for temporary data storage during image reconstruction.

The X-ray controller 22 and the gantry motor controller 23 are connected to a computer 25 such as a Data General Eclipse MV/7800C general purpose minicomputer. The computer 25 also provides control signals and data to DAS 24 via buses 29. The computer 25 receives commands and scanning parameters via an operator console 27 having a cathode ray tube display and keyboard that allow the operator to enter parameters for the scan and to observe the reconstructed image and other information from the computer. A mass storage device 28 provides a means for storing operating programs for the CT imaging system, as well as image data for future reference by the operator.

During X-ray data acquisition, the gantry 12 typically makes one complete revolution around the object 15 being imaged, although the present invention can be utilized in CT systems which acquire data while the gantry moves 180 degrees plus the angle of the fan-shaped beam pattern. The present acquisition process involves acquiring a first set of projections in which the gantry moves a distance equivalent to the pitch of the detectors 18 between each projection. A similar second set of projections also is acquired in which the projections are shifted by an odd multiple of one-half the detector pitch from the projections in the first set. Preferably the projections are shifted by only one-half the detector pitch and this version of the present invention will be described.

Although all of the projections in the first set can be acquired during one scan with the second set of projections being acquired thereafter during a second revolution of the gantry, movement of the imaged object during this sequential scanning has an adverse affect on the reconstructed image.

The preferred data acquisition technique is to acquire both sets of transmission profile data during a single revolution of the gantry. Data for a first projection is read from the detectors 18 while the gantry 12 is in a position denoted by the solid lines in FIG. 4. To simplify the illustration only three detectors 18 are shown. Individual X-ray beams are portrayed by solid lines 41 emanating from a first focal spot on the anode of the X-ray source 13 and located at position 40 with respect to the object. The transmission profile data for this projection is acquired by sampling the output signal from each detector in the array 20. The projection data then is processed by the DAS 24 and stored temporarily in a memory of the image reconstructor 26.

Figure 4:
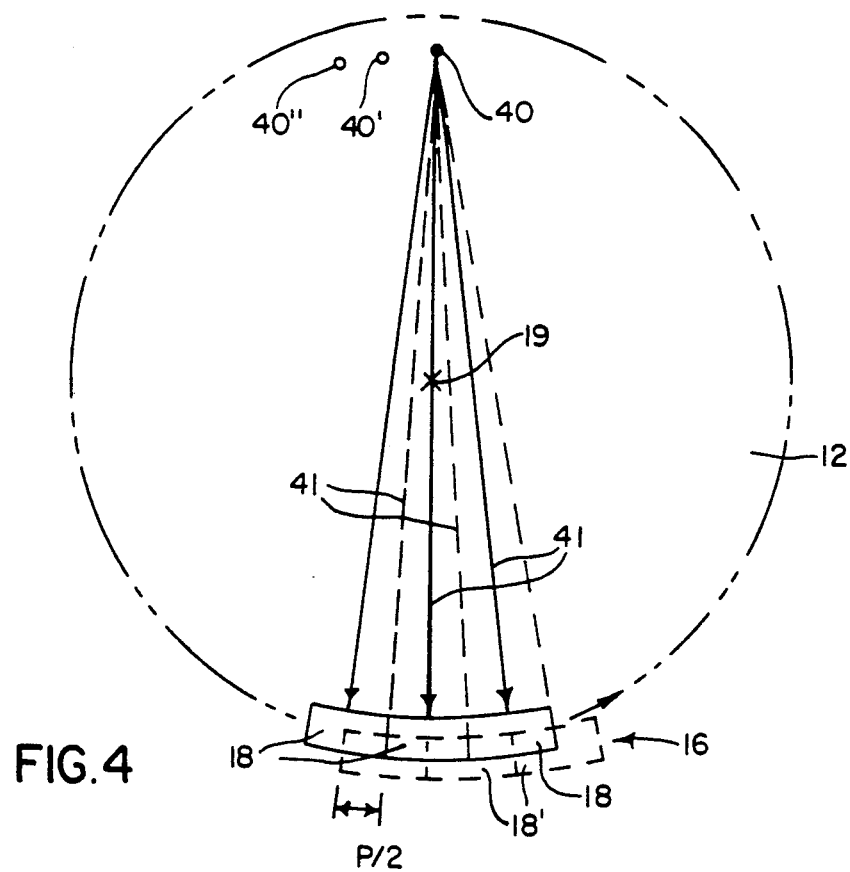
FIG. 4 illustrates the relative position of the focal spot and the detectors during two consecutively acquired projections.

Then the gantry and the detector array mounted thereon rotates one-half the pitch (P) of the detectors 18 into a second position denoted by the dashed lines in FIG. 4. At this gantry position the first focal point of the X-ray source 13 moves into a point designated by 40'. However, the electron beam within the X-ray source is deflected to a second focal spot on the anode which is located at the position 40 where the first focal spot was during the previous projection. X-ray beams emanating from this "wobbled" focal spot which align with the centers of the detectors 18' are depicted by dashed lines 41'. The transmission profile data for this second projection is processed by the DAS 24 and fed to the image reconstructor 26.

The gantry 12 continues to move another amount equal to one-half the detector pitch (P). At this point, the electron beam in the X-ray source 13 is deflected to strike the anode at the first focal spot which has moved to position 40". In this orientation of the gantry, data for another projection in the second data array is acquired and stored in a memory of the image reconstructor 26. This process continues alternately to acquire projection data in an interleaved fashion until the gantry 12 completes a scan of the imaged object 15 at which time two sets of projection have been acquired.

The preferred process described above acquires the two sets of projections in a time interleaved manner during a single revolution of the gantry. Alternatively, the two sets of projections could be acquired sequentially during separate revolutions of the gantry. In this latter case, the focal spot is wobbled once, between the two revolutions.

Figure 5:
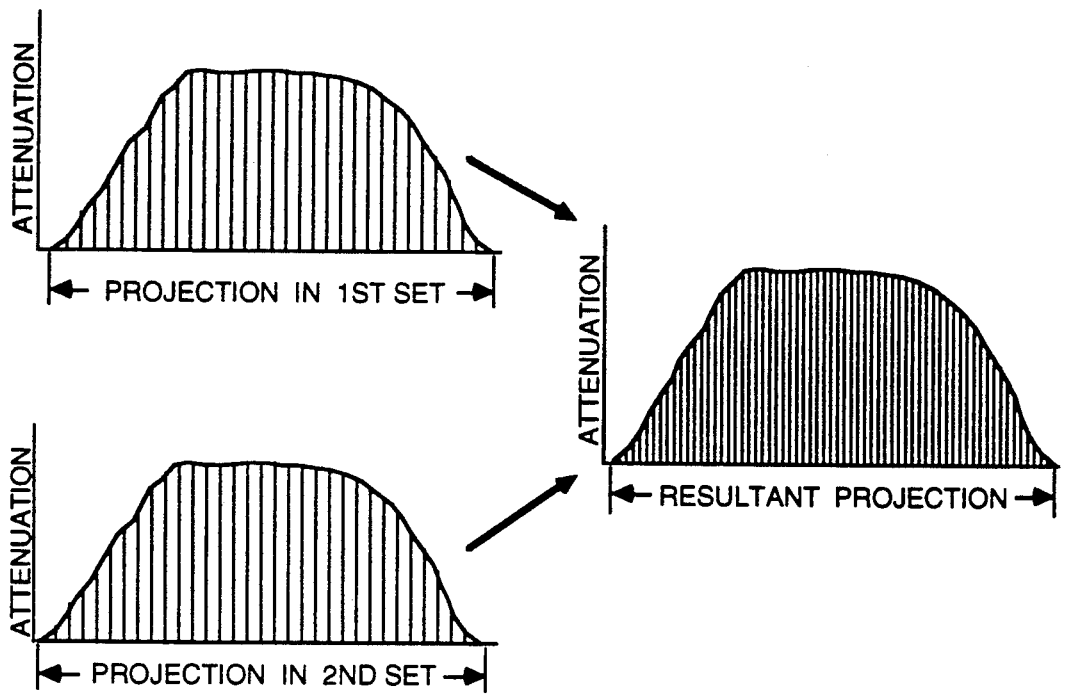
FIG. 5 depicts the process of interleaving two sets of detector data into a combined set for use in reconstructing an image.

As a pair of adjacent projections have been acquired, the image reconstructor 26 interleaves the samples acquired from each detector in the two projections. In this process, shown schematically in FIG. 5, the sample from the first detector in one projection is inserted between samples from the first and second detectors in the other projection. The sample from the second detector in the one projection is inserted between samples from the second and third detectors in the other projection; and so on. The combined projection that results from this process has twice the number of data samples as each original projection. The data for the combined projection are stored in another array in the memory of the image reconstructor 26 and the combining step is repeated for each pair of acquired projections.

Alternatively, the two sets of projections can be stored separately in the image reconstructor 26. In this case the two sets can be filtered at an an appropriate cut-off frequency and then the two sets of projections are interleaved.

The combined projections for the entire scan then are employed to reconstruct an image using a conventional technique, such as filtered backprojection. The reconstructed image is displayed by the computer 25 on a video monitor of the operator console 27. The image data may also be archived in the mass storage device 28.

The invention being claimed is:

1. A method of producing an image with a tomographic imaging system having an X-ray source opposed to a plurality of periodically spaced X-ray detectors mounted on a gantry rotatable about an object being imaged, and the system being useable to acquire a series of projections each of which being formed by signals from the detectors at different angular positions with respect to the object; steps of the method comprising:

rotating the gantry around the object;
acquiring a first set of projections as the gantry moves through an angular segment when the source emitting X-rays from a first focal spot;
acquiring a second set of projections as the gantry moves through the angular segment with the source emitting X-rays from a second focal spot, where each projection in the second set is interlaced physically with a projection in the first set;
filtering the first set of projections to produce a first filtered set of projections;
filtering the second set of projections to produce a second filtered set of projections;
combining the first and second filtered sets of projections into a resultant group of projections; and
reconstructing an image from the resultant group of projections.

2. The method as recited in claim 1 wherein each projection in the second set of projections is acquired when the gantry is at a position that is offset by substantially an odd multiple of one-half the periodic spacing of the X-ray detectors from a position of the gantry at which a projection in the first set was acquired.

3. The method as recited in claim 1 wherein each projection in the resultant group is formed by interleaving data samples of a projection in one set with data samples of a projection in the other set.

4. The method as recited in claim 1 wherein said step of combining the first and second filtered sets of projections into a resultant group of projections comprises alternately selecting a data sample from the first and second filtered sets of projections.

5. The method as recited in claim 1 wherein said steps of acquiring the first and second sets of projections occur interleaved in time as the gantry makes a single pass through the angular segment.

6. The method as recited in claim 1 wherein said steps of acquiring the first and second sets of projections occur sequentially in time during separate passes of the gantry through the angular segment.

7. A method of producing an image with a tomographic imaging system having an X-ray source opposed to a plurality of periodically spaced X-ray detectors mounted on a gantry rotatable about an object being imaged, and the system being useable to acquire a series of projections of the object with each projection being formed by signals from the detectors at different angular positions of the gantry; steps of the method comprising:

(a) operating the X-ray source to emit X-rays from a first focal spot;
(b) acquiring one projection while the source emits X-rays from the first focal spot which one projection is stored in a first data array;
(c) altering the operation of the source to emit X-rays from a second focal spot;
(d) rotating the gantry by an amount which moves the detectors by an odd multiple of one-half of the periodic spacing;

(e) acquiring another projection while the source emits X-rays from the second focal spot which other projection is stored in a second data array;

(f) rotating the gantry by an amount which moves the detectors by an odd multiple of one-half the periodic spacing;

(g) repeating steps (a) through (f) until a plurality of the projections have been acquired in each of the first and second data arrays, and thereafter;

(h) filtering the first data array to produce a first filtered data array;

(i) filtering the second set of projections to produce a second filtered data array;

(j) combining the first and second filtered data arrays by interleaving data samples of the projections in each array to produce a resultant data array; and (k) reconstructing an image from the resultant data array.

8. A computed tomography apparatus for imaging an object comprising:

a gantry rotatable about the object;

an X-ray source mounted on said gantry for producing X-ray beams from first and second focal spots generally within a plane of rotation of the gantry;

an array comprising a plurality detectors periodically spaced at a distance P for sensing radiation received from the X-ray source in the form of image projections;

an X-ray controller causing emission of X-rays from the X-ray source to shift between the two focal spots to produce first and second sets of projection data;

a gantry controller to coordinate rotation of the gantry with shifting of the X-ray emission from source so that the first and second sets of projection data are interlaced; and an image reconstructor which interleaves data samples of the first set of projection data with data samples of the second set of projection data to form a resultant set of projection data, and then reconstructs an image from the resultant set of projection data.

9. The computer tomography apparatus as recited in claim 8 wherein gantry controller rotates the gantry so that projections in the first set are offset from projections in the second set by a distance substantially equal to one-half distance P.

10. The computed tomography apparatus as recited in claim 8 wherein the first and second sets of projection data are acquired while the gantry makes a single pass through an angular segment of rotation.

11. The computed tomography apparatus as recited in claim 8 wherein the first and second sets of projection data are acquired sequentially in time while the gantry makes separate passes through an angular segment of rotation.

* * * * *